United States Patent
Schadt et al.

(10) Patent No.: US 9,481,668 B2
(45) Date of Patent: Nov. 1, 2016

(54) QUINOLINE INHIBITOR OF THE MACROPHAGE STIMULATING 1 RECEPTOR MSTR1

(71) Applicant: Merck Patent GmbH, Darmstadt (DE)

(72) Inventors: Oliver Schadt, Rodenbach (DE); Christina Esdar, Mainz (DE); Carsten Schultz-Fademrecht, Dortmund (DE); Jan Eickhoff, Heerdecke (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/895,952

(22) PCT Filed: May 7, 2014

(86) PCT No.: PCT/EP2014/001231
§ 371 (c)(1),
(2) Date: Dec. 4, 2015

(87) PCT Pub. No.: WO2014/194975
PCT Pub. Date: Dec. 11, 2014

(65) Prior Publication Data
US 2016/0115154 A1 Apr. 28, 2016

(30) Foreign Application Priority Data
Jun. 6, 2013 (EP) .................................. 13002926

(51) Int. Cl.
A61K 31/506 (2006.01)
C07D 401/14 (2006.01)
C07D 239/28 (2006.01)
A61K 31/4709 (2006.01)
A61K 45/06 (2006.01)

(52) U.S. Cl.
CPC .......... *C07D 401/14* (2013.01); *A61K 31/4709* (2013.01); *A61K 31/506* (2013.01); *A61K 45/06* (2013.01)

(58) Field of Classification Search
CPC . A61K 31/506; C07D 401/14; C07D 239/28
USPC ......................................... 514/256; 544/322
See application file for complete search history.

(56) References Cited

U.S. PATENT DOCUMENTS

| 7,858,623 B2 | 12/2010 | Kim et al. |
| 8,088,794 B2 | 1/2012 | Kim et al. |
| 8,685,983 B2 | 4/2014 | Kim et al. |
| 8,999,982 B2 | 4/2015 | Schultz-Fademrecht et al. |
| 2008/0312232 A1 | 12/2008 | Kim et al. |
| 2011/0053931 A1 | 3/2011 | Gaudino et al. |
| 2011/0118252 A1 | 5/2011 | Kim et al. |
| 2012/0070413 A1 | 3/2012 | Kim et al. |
| 2014/0018365 A1 | 1/2014 | Schultz-Fademrecht et al. |

FOREIGN PATENT DOCUMENTS

| EP | 2423208 A1 | 2/2012 |
| WO | 2006/116713 A1 | 11/2006 |
| WO | 2007/146824 A2 | 12/2007 |

OTHER PUBLICATIONS

Zhang, J et al, Cancer Research (2008), vol. 68, pp. 6680.*
International Search Report dated Sep. 9, 2014 issued in corresponding PCT/EP2014/001231 application (pp. 1-4).
L. Liu et al., "Discovery of a Potent, Selective, and Orally Bioavailablec-MetInhibitor:1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458)", Journal of Medicinal Chemistry, vol. 51 (2008) pp. 3688-3691.
S. Raeppel et al., "Identification of a Novel Series of Potent RON Receptor Tyrosine Kinase Inhibitors", Bioorganic & Medicinal Chemistry Letters, vol. 20, No. 9 (2010) pp. 2745-2749.
J. Porter, "Small Molecule c-Met Kinase Inhibitors: A Review of Recent Patents", Expert Opinion on Therapeutic Patents, vol. 20, No. 2 (2010) pp. 159-177.
T.L. Underiner et al., "Discovery of Small Molecule c-Met Inhibitors: Evolution and Profiles of Clinical Candidates", Anti-Cancer Agents in Medicinal Chemistry, vol. 10, No. (2010) pp. 7-27.

* cited by examiner

*Primary Examiner* — Kamal Saeed
*Assistant Examiner* — Janet L Coppins
(74) *Attorney, Agent, or Firm* — Millen White Zelano and Branigan, PC; John Sopp; Anthony Zelano

(57) ABSTRACT

The compound N-(4-((6,7-dimethoxyquinolin-4-yl)oxy)-3-fluorophenyl)-5-ethyl-1 -(pyrimidin-5-yl)-1H-pyrazole-4-carboxamide

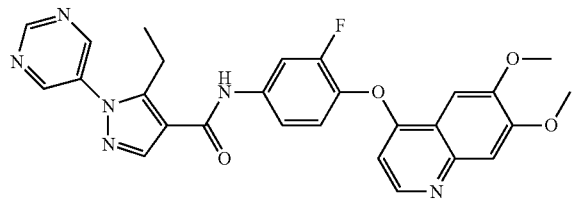

and pharmaceutically usable salts, tautomers and stereoisomers thereof, including mixtures thereof in all ratios, is an inhibitor of RON and can be employed, for the treatment of cancer.

3 Claims, No Drawings

QUINOLINE INHIBITOR OF THE MACROPHAGE STIMULATING 1 RECEPTOR MSTR1

BACKGROUND OF THE INVENTION

The invention had the object of finding novel compounds having valuable properties, in particular those which can be used for the preparation of medicaments.

The present invention relates to the compound N-(4-((6,7-dimethoxyquinolin-4-yl)oxy)-3-fluorophenyl)-5-ethyl-1-(pyrimidin-5-yl)-1H-pyrazole-4-carboxamide that is capable of inhibiting one or more kinases. The compound find applications in the treatment of a variety of disorders, including cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The present invention relates to N-(4-((6,7-dimethoxyquinolin-4-yl)oxy)-3-fluorophenyl)-5-ethyl-1-(pyrimidin-5-yl)-1H-pyrazole-4-carboxamide and to the use of N-(4-((6,7-dimethoxyquinolin-4-yl)oxy)-3-fluorophenyl)-5-ethyl-1-(pyrimidin-5-yl)-1H-pyrazole-4-carboxamide in which the inhibition, regulation and/or modulation of signal transduction by kinases, in particular receptor tyrosine kinases, plays a role, furthermore to pharmaceutical compositions which comprise the compound, and to the use of the compound for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

In particular, the present invention relates to N-(4-((6,7-dimethoxyquinolin-4-yl)oxy)-3-fluorophenyl)-5-ethyl-1-(pyrimidin-5-yl)-1H-pyrazole-4-carboxamide and to the use of N-(4-((6,7-dimethoxyquinolin-4-yl)oxy)-3-fluorophenyl)-5-ethyl-1-(pyrimidin-5-yl)-1H-pyrazole-4-carboxamide in which the inhibition, regulation and/or modulation of signal transduction by RON (récepteur d'origine nantais) plays a role.

One of the principal mechanisms by which cellular regulation is effected is through the transduction of extracellular signals across the membrane, that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

S. Raeppel et al. describe potent RON receptor tyrosine kinase inhibitors with residual activity against the closely related c-Met or potent dual inhibitory activity against RON and c-Met, such as N-(3-fluoro-4-(2-substituted-thieno[3,2-b]pyridine-7-oxy)phenyl)-1-phenyl-5-(trifluoromethyl)-1H-pyrazole-4-carboxamides, in Bioorganic & Medicinal Chemistry Letters 20 (2010) 2745-2749 as potential anticancer therapeutics.

ImClone Systems (now a division of Eli Lilly & Co.) developed IMC-41A10, a human IgG1 monoclonal antibody that binds with high affinity to human RON RTK (receptor tyrosine kinase) and blocks MSP (macrophage stimulating protein) ligand binding (J. M. O'Toole et al., Cancer Res. 2006, 66, 9162). IMC-41A10 inhibited tumor growth by 50-60% in several human xenograft tumor models including colon, lung and pancreatic carcinoma models.

Small molecule inhibitors of RON have been described as well. These chemical entities inhibit both RON and the closely related c-Met kinase. c-Met is found to be activated in a large number of different cancers and small molecule inhibitors targeting Met/RON are presently under clinical evaluation in patients with solid tumors:

(a) For recent reviews see: P. C. Ma, G. Maulik, J. Christensen and R. Salgia, *Cancer Metastasis Rev.* 22 (2003), p. 309.
(b) C. W. Birchmeier, W. Birchmeier, E. Gherardi and G. F. Vande Woude, *Nat. Rev. Mol. Cell Biol.* 4 (2003), p. 915.
(c) J. G. Christensen, J. Burrows and R. Salgia, *Cancer Lett.* 225 (2005), p. 1.
(d) S. Corso, P. M. Comoglio and S. Giordano, *Trends Mol. Med.* 11 (2005), p. 284.
(e) C. Boccaccio and P. M. Comoglio, *Nat. Rev. Cancer* 6 (2006), p. 637.
(f) B. Peruzzi and D. P. Bottaro, *Clin. Cancer Res.* 12 (2006), p. 3657.
(g) B. S. Knudsen and G. Vande Woude, *Cur. Opin. Gen. Dev.* 18 (2008), p. 87.
(h) L. Toschi and P. A. Jänne, *Clin. Cancer Res.* 14 (2008), p. 5941.
(i) I. Dussault and S. F. Belton, *Anti-Cancer Agents Med. Chem.* 9 (2009), p. 221.
(j) N. A. Cipriani, O. O. Abidoye, E. Vokes and R. Salgia, *Lung Cancer* 63 (2009), p. 169.
(k) J. Porter, *Expert Opin. Ther. Patents* 20 (2010), p. 159.
(l) T. L. Underiner, T. Herbertz and S. J. Miknyoczki, *Anti-Cancer Agents Med. Chem.* 10 (2010), p. 7.

For example, a potent small-molecule dual inhibitor of c-Met/RON was disclosed by Amgen:

J. Zhang et al., Cancer Res. 2008, 68, 6680;
L. Liu et al., J. Med. Chem. 2008, 51, 3688.

This quinoline based compound having the 1-(2-hydroxy-2-methylpropyl)-5-methyl-3-oxo-2-phenyl-2,3-dihydro-1H-pyrazole-4-carboxamide head group

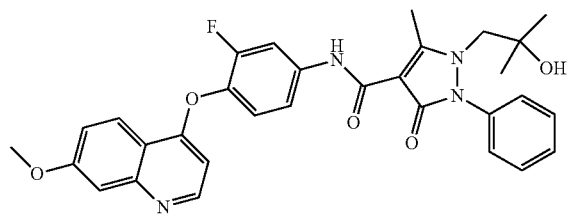 [SMILES: COc1ccc2c(Oc3ccc(NC(=O)c4c(C)n(CC(C)(C)O)n(-c5ccccc5)c4=O)cc3F)ccnc2c1]

inhibits both Met and RON enzymes and demonstrates anti-tumor activity in a colorectal xenograft model in mice.

Bristol-Myers Squib describes BMS-777607

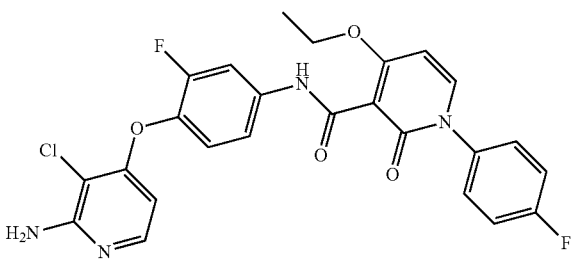 [SMILES: CCOc1ccn(-c2ccc(F)cc2)c(=O)c1C(=O)Nc1ccc(Oc2ccnc(N)c2Cl)c(F)c1]

as a new pyridine based selective and orally efficacious inhibitor of the Met/RON kinase superfamily that has advanced into phase I clinical trials (G. M. Schroeder et al., J. Med. Chem. 2009, 52, 1251).

Accordingly, the compound according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compound according to the invention is furthermore suitable for the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to the compound according to the invention as medicament and/or medicament active ingredient in the treatment and/or prophylaxis of the said diseases and to the use of the compound according to the invention for the preparation of a pharmaceutical for the treatment and/or prophylaxis of the said diseases and to a process for the treatment of the said diseases comprising the administration of the compound according to the invention to a patient in need of such an administration.

It can be shown that the compound according to the invention has an antiproliferative action. The compound according to the invention is administered to a patient having a hyperproliferative disease, for example to inhibit tumour growth, to reduce inflammation associated with a lymphoproliferative disease, to inhibit transplant rejection or neurological damage due to tissue repair, etc. The present compound is suitable for prophylactic or therapeutic purposes. As used herein, the term "treatment" is used to refer to both the prevention of diseases and the treatment of pre-existing conditions. The prevention of proliferation/vitality is achieved by administration of the compound according to the invention prior to the development of overt disease, for example for preventing tumour growth. Alternatively, the compound is used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined. The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compound according to the invention is suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions.

Occlusive graft vascular diseases of interest include atherosclerosis, coronary vascular disease after grafting, vein graft stenosis, perianastomatic prosthetic restenosis, restenosis after angioplasty or stent placement, and the like.

In addition, the compound according to the invention can be used to achieve additive or synergistic effects in certain existing cancer chemotherapies and radiotherapies and/or to restore the efficacy of certain existing cancer chemotherapies and radiotherapies.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing the compound of the present invention and a target kinase together in such a manner that the compound can affect the enzyme activity of the kinase either directly; i.e., by interacting with the kinase itself or indirectly; i.e., by interacting with another molecule on which the catalytic activity of the kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

For the compound used in this invention, a therapeutically effective amount, also referred to herein as a therapeutically effective dose, can be estimated initially from cell culture assays. For example, a dose can be formulated in animal models to achieve a circulating concentration range that includes the IC50 or the IC100 as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the LD50 and the ED50. The dose ratio between toxic and therapeutic effect is the therapeutic index and can be expressed as the ratio between LD50 and ED50. The data obtained from these cell cultures assays and animal studies can be used in formulating a dosage range that is not toxic for use in human. The dosage lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition, (see, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day.

Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

Preferred diseases or disorders that the compound described herein may be useful in preventing, treating and/or studying are cell proliferative disorders, especially cancer such as, but not limited to, papilloma, blastoglioma, Kaposi's sarcoma, melanoma, lung cancer, ovarian cancer, prostate cancer, squamous cell carcinoma, astrocytoma, head cancer, neck cancer, skin cancer, liver cancer, bladder cancer, breast cancer, lung cancer, uterus cancer, prostate cancer, testis carcinoma, colorectal cancer, thyroid cancer, pancreatic cancer, gastric cancer, hepatocellular carcinoma, leukemia, lymphoma, Hodgkin's disease and Burkitt's disease.

PRIOR ART

Other heterocyclic derivatives and their use as anti-tumour agents have been described in WO 2006/116713 A1.

S. Raeppel et al. describe potent RON receptor tyrosine kinase inhibitors in Bioorganic & Medicinal Chemistry Letters 20 (2010) 2745-2749 as potential anti-cancer therapeutics.

SUMMARY OF THE INVENTION

The invention relates to the compound N-(4-((6,7-dimethoxyquinolin-4-yl)oxy)-3-fluorophenyl)-5-ethyl-1-(pyrimidin-5-yl)-1H-pyrazole-4-carboxamide

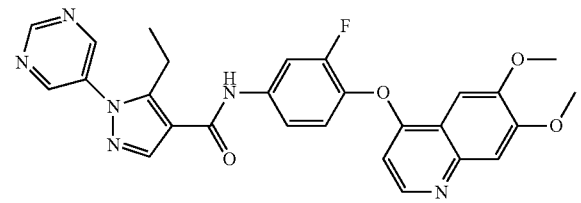 [SMILES: CCc1c(C(=O)Nc2ccc(Oc3ccnc4cc(OC)c(OC)cc34)c(F)c2)cnn1-c1cncnc1]

and pharmaceutically usable salts, tautomers and stereoisomers thereof, including mixtures thereof in all ratios.

The invention also relates to the optically active forms (stereoisomers), salts, the enantiomers, the racemates, the diastereomers and the hydrates and solvates of the compound. The term solvates of the compound is taken to mean adductions of inert solvent molecules onto the compounds which form owing to their mutual attractive force. Solvates are, for example, mono- or dihydrates or alkoxides.

Of course, the invention also relates to the solvates of the salts.

The term pharmaceutically usable derivatives is taken to mean, for example, the salts of the compound according to the invention and also so-called prodrug compounds. The term prodrug derivatives is taken to mean the compound according to the invention which has been modified by means of, for example, alkyl or acyl groups, sugars or oligopeptides and which is rapidly cleaved in the organism to form the effective compound according to the invention.

These also include biodegradable polymer derivatives of the compound according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention relates to N-(4-((6,7-dimethoxyquinolin-4-yl)oxy)-3-fluorophenyl)-5-ethyl-1-(pyrimidin-5-yl)-1H-pyrazole-4-carboxamide and salts thereof and to a process for the preparation of N-(4-((6,7-dimethoxyquinolin-4-yl)oxy)-3-fluorophenyl)-5-ethyl-1-(pyrimidin-5-yl)-1H-pyrazole-4-carboxamide and pharmaceutically usable salts, tautomers and stereoisomers thereof, characterised in that

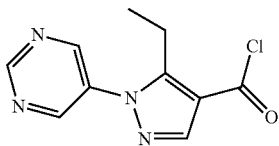 [SMILES: CCc1c(C(=O)Cl)cnn1-c1cncnc1]

is reacted with

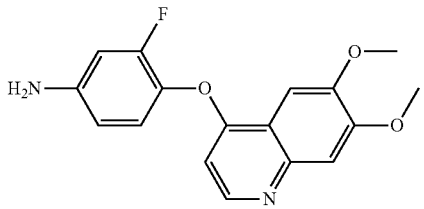 [SMILES: COc1cc2nccc(Oc3ccc(N)cc3F)c2cc1OC]

and/or

N-(4-((6,7-dimethoxyquinolin-4-yl)oxy)-3-fluorophenyl)-5-ethyl-1-(pyrimidin-5-yl)-1H-pyrazole-4-carboxamide is converted into one of its salts.

N-(4-((6,7-dimethoxyquinolin-4-yl)oxy)-3-fluorophenyl)-5-ethyl-1-(pyrimidin-5-yl)-1H-pyrazole-4-carboxamide and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

N-(4-((6,7-dimethoxyquinolin-4-yl)oxy)-3-fluorophenyl)-5-ethyl-1-(pyrimidin-5-yl)-1H-pyrazole-4-carboxamide can preferably be obtained by reacting 5-ethyl-1-pyrimidin-5-yl-pyrazole-4-carbonyl chloride with 4-[(6,7-dimethoxy-4-quinolyl)oxy]-3-fluoro-aniline.

In 5-ethyl-1-pyrimidin-5-yl-pyrazole-4-carbonyl chloride the Cl may be replaced by Br, I or a free or reactively modified OH group, such as, for example, an activated ester, an imidazolide or alkylsulfonyloxy having 1-6 C atoms (preferably methyl-sulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°. Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to pyridine, acetonitrile, dichloromethane and/or DMF.

Pharmaceutical Salts and Other Forms

The said compound according to the invention can be used in its final non-salt form. On the other hand, the present invention also encompasses the use of the compound in the form of its pharmaceutically acceptable salts, which can be derived from various organic and inorganic acids and bases by procedures known in the art.

Pharmaceutically acceptable salt forms of the compound according to the invention are for the most part prepared by conventional methods. In the case of N-(4-((6,7-dimethoxyquinolin-4-yl)oxy)-3-fluorophenyl)-5-ethyl-1-(pyrimidin-5-yl)-1H-pyrazole-4-carboxamide, acid-addition salts can be formed by treating the compound with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compound include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentane-propionate, digluconate, dihydrogenphosphate, dinitrobenzoate, dodecylsulfate, ethanesulfonate, fumarate, galacterate (from mucic acid), galacturonate, gluco-heptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of N-(4-((6,7-dimethoxyquinolin-4-yl)oxy)-3-fluorophenyl)-5-ethyl-1-(pyrimidin-5-yl)-1H-pyrazole-4-carboxamide are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

With regard to that stated above, it can be seen that the expression "pharmaceutically acceptable salt" in the present connection is taken to mean an active ingredient which comprises N-(4-((6,7-dimethoxyquinolin-4-yl)oxy)-3-fluorophenyl)-5-ethyl-1-(pyrimidin-5-yl)-1H-pyrazole-4-carboxamide in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least N-(4-((6,7-dimethoxyquinolin-4-yl)oxy)-3-fluorophenyl)-5-ethyl-1-(pyrimidin-5-yl)-1H-pyrazole-4-carboxamide and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

N-(4-((6,7-dimethoxyquinolin-4-yl)oxy)-3-fluorophenyl)-5-ethyl-1-(pyrimidin-5-yl)-1H-pyrazole-4-carboxamide and the pharmaceutically usable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

N-(4-((6,7-dimethoxyquinolin-4-yl)oxy)-3-fluorophenyl)-5-ethyl-1-(pyrimidin-5-yl)-1H-pyrazole-4-carboxamide and the pharmaceutically usable salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compound may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouth-washes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of N-(4-((6,7-dimethoxyquinolin-4-yl)oxy)-3-fluorophenyl)-5-ethyl-1-(pyrimidin-5-yl)-1H-pyrazole-4-carboxamide depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least N-(4-((6,7-dimethoxyquinolin-4-yl)oxy)-3-fluorophenyl)-5-ethyl-1-(pyrimidin-5-yl)-1H-pyrazole-4-carboxamide and/or the pharmaceutically usable salts, tautomers and stereoisomers thereof, including mixtures thereof in all ratios, and at least one further medicament active ingredient.

The invention also relates to a set (kit) consisting of separate packs of (a) an effective amount of N-(4-((6,7-dimethoxyquinolin-4-yl)oxy)-3-fluorophenyl)-5-ethyl-1-(pyrimidin-5-yl)-1H-pyrazole-4-carboxamide and/or the pharmaceutically usable salts, tautomers and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount N-(4-((6,7-dimethoxyquinolin-4-yl)oxy)-3-fluorophenyl)-5-ethyl-1-(pyrimidin-5-yl)-1H-pyrazole-4-carboxamide and/or the pharmaceutically usable salts, tautomers and stereoisomers thereof, including mixtures thereof in all ratios, and an effective amount of a further medicament active ingredient in dissolved or lyophilised form.

Use

The invention relates to N-(4-((6,7-dimethoxyquinolin-4-yl)oxy)-3-fluorophenyl)-5-ethyl-1-(pyrimidin-5-yl)-1H-pyrazole-4-carboxamide for the use for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to the use of N-(4-((6,7-dimethoxyquinolin-4-yl)oxy)-3-fluorophenyl)-5-ethyl-1-(pyrimidin-5-yl)-1H-pyrazole-4-carboxamide for the preparation of a medicament for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to a method of treating a mammal having a disease selected from cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease, wherein the method comprises administering to a mammal a therapeutically effective amount of N-(4-((6,7-dimethoxyquinolin-4-yl)oxy)-3-fluorophenyl)-5-ethyl-1-(pyrimidin-5-yl)-1H-pyrazole-4-carboxamide.

N-(4-((6,7-Dimethoxyquinolin-4-yl)oxy)-3-fluorophenyl)-5-ethyl-1-(pyrimidin-5-yl)-1H-pyrazole-4-carboxamide is suitable as pharmaceutical active ingredients for mammals, especially for humans, in the treatment and control of cancer diseases and inflammatory diseases.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compound according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

The present invention encompasses the use of N-(4-((6,7-dimethoxyquinolin-4-yl)oxy)-3-fluorophenyl)-5-ethyl-1-(pyrimidin-5-yl)-1H-pyrazole-4-carboxamide and/or physiologically acceptable salts, tautomers and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of N-(4-((6,7-dimethoxyquinolin-4-yl)oxy)-3-fluorophenyl)-5-ethyl-1-(pyrimidin-5-yl)-1H-pyrazole-4-carboxamide and/or physiologically acceptable salts, tautomers and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the cancer disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

N-(4-((6,7-Dimethoxyquinolin-4-yl)oxy)-3-fluorophenyl)-5-ethyl-1-(pyrimidin-5-yl)-1H-pyrazole-4-carboxamide may also be administered at the same time as other well-known therapeutic agents that are selected for their particular usefulness against the condition that is being treated.

The present compound is also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenyl-hydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamine-platinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(di-methylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylene-dioxy)-5-methyl-7-hydroxy-8-methoxybenzo[c]phenanthridinium, 6,9-bis[(2-amino-ethyl)amino]benzo[g]isoquinoline-5,10-dione, 5-(3-aminopropylamino)-7,10-dihydroxy-2-(2-hydroxyethylaminomethyl)-6H- pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Test for the Inhibition of RON

Inhibition of MSP (Macrophage Stimulating Protein) Induced pRON in Cellular Assays To determine potency and efficacy of RON kinase inhibitors in inhibiting ligand induced RON phosphorylation, N-(4-((6,7-dimethoxyquinolin-4-yl)oxy)-3-fluorophenyl)-5-ethyl-1-(pyrimidin-5-yl)-1H-pyrazole-4-carboxamide was tested in cell based assays as described below. Inhibition of ligand induced pRON (phosphoRON) in MDA-MB453 cells (cell based electrochemiluminescence assay (ECLA)): MDA-MB453 cells (DSMZ ACC65) were serum starved, pretreated with 100IM Sodium Orthovanadate (1 h, 37° C., 5% $CO_2$) and pre-incubated with compounds (serial dilutions, starting concentration 30 µM) in serum-free media for 45 min at 37° C., 5% $CO_2$. Cells were stimulated with 250 ng/ml MSP (R&D Systems, #4306-MS) for 20 min, supernatants discarded and cells lysed in cold NP-40 lysis buffer (1% NP-40, 20 mM Tris, pH8.0, 137 mM NaCl, 10% glycerole, 2 mM EDTA, protease inhibitor cocktail set III (Calbiochem), phosphatase inhibitor cocktail set II (Calbiochem)). MA6000 96 well plates (MSD, # L15XB) were blocked with 3% block A (MSD) in PBS, pH7.4, 0.05% Tween20 and coated with RON specific capture antibody (R&D Systems, # MAB691). Cell lysates were added and incubated for 2 h at room temperature (RT). Biotinylated anti-phospho Tyrosine antibody (R&D Systems, # BAM1676) and sulfo tag streptavidin reagent (MSD, #R32AD) were used for detection.

In-Vitro (Enzyme) Assay for Determination of the Efficacy of Inhibitors of RON Kinase-Mediated Effects The kinase assay was carried out as 384-well FlashPlate assay. As test plates 384-well streptavidine coated FlashPlate microtitre plates from Perkin Elmer (USA) were used. The components of the kinase reaction were pipetted into the assay plate. 4.5 nM of GST tagged human recombinant RON kinase (Life technologies), 500 nM of biotinylated peptide substrate RDILDREYYSVQQHRH-amide (autophosphorylation site derived peptide substrate, custom-made) and 2 µM of ATP (with 0.5 µCi of <33>P-ATP/well) were incubated in a total volume of 50 µl (50 mM of HEPES, 5 mM of $MgCl2$, 2 mM of DTT, 0.1% of BSA, 0.01% Igepal®CA630, 1% DMSO, pH 7.5) in the presence or absence of test substance (10 concentrations) at 22 [deg.] C for 30 min. The reaction was stopped using 50 µl of 200 mM EDTA solution. After incubation for a further 80 min at room temperature, the supernatants were removed by suction, and the wells were washed three times with 100 µl of 0.9% NaCl solution each time. The radioactivity was measured using a Topcount scintillation counter (PerkinElmer, USA). The $IC_{50}$ values were calculated using Assay explorer (Table X).

The preparation of N-(4-((6,7-dimethoxyquinolin-4-yl) oxy)-3-fluorophenyl)-5-ethyl-1-(pyrimidin-5-yl)-1H-pyrazole-4-carboxamide is carried out analogously to the following Scheme 1.

5-Hydrazinylpyrimidine A2 is obtained by copper-catalyzed reaction of pyrimidine-5-boronic acid with di-tert-butyl-azodicarboxylate. Subsequent reaction of A2 with A1 yields the pyrazole A3. Finally, hydrolysis of A3 and subsequent acid chloride formation yields A5. The reaction of aniline 1 and acid chloride A5 is carried out in the presence of a base like pyridine and optionally in an inert solvent like DCM. The acid chloride A5 can be prepared from the carboxylic acid via standard procedures, using thionyl chloride or oxalyl chloride as reagents. Alternatively, carboxylic acid A4 can be directly coupled with aniline 1 under standard procedures, such as using HBTU or HATU to give A6.

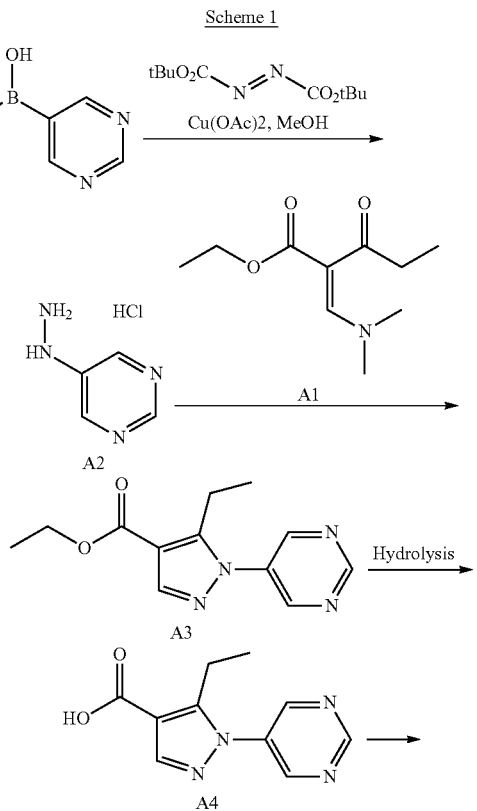

Scheme 1

-continued

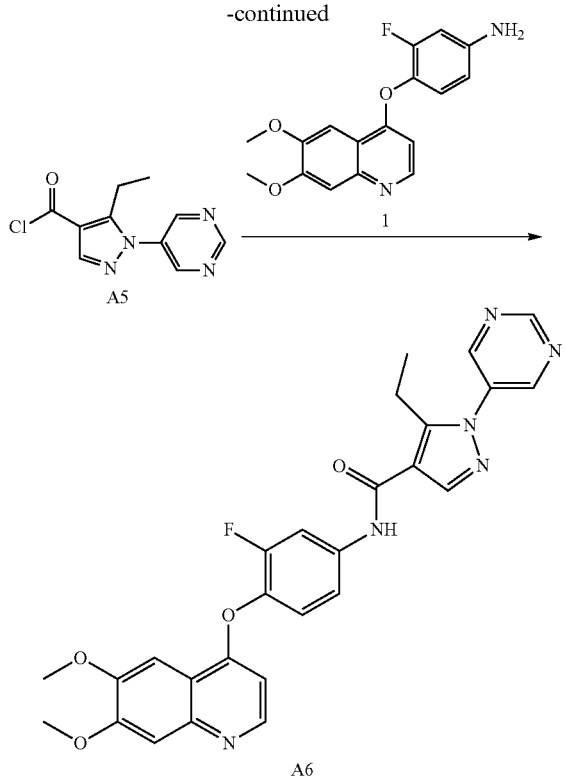

Preparation of N-(4-((6,7-dimethoxyquinolin-4-yl)oxy)-3-fluorophenyl)-5-ethyl-1-(pyrimidin-5-yl)-1H-pyrazole-4-carboxamide Abbreviations used in the description of the chemistry and in the Example that follow are:

ACN (acetonitrile); br (broad); CDCl$_3$ (deuterated chloroform); DCM (dichloromethane); DMF (dimethylformamide); DMSO (dimethyl sulfoxide); eq. (equivalent); ES (electrospray); EtOAc (ethyl acetate); EtOH (ethanol); HCl (hydrochloric acid); HOAc (acetic acid); KOH (potassium hydroxide); MeOH (methanol); MS (mass spectrometry); NaHCO$_3$ (sodium hydrogencarbonate); NMR (nuclear magnetic resonance; PE (petroleum ether); RT (room temperature); sat. aq. (saturated aqueous); SiO$_2$ (silica gel); THF (tetrahydrofuran).

Step 1: Ethyl 2-((dimethylamino)methylene)-3-oxopentanoate (A1)

N,N-Dimethylformamide dimethyl acetal (19.9 g, 166.5 mmol, 1.2 eq.) was slowly added to 3-oxopentanoic acid ethyl ester (20 g, 139 mmol, 1.0 eq.) at RT. After stirring for 24 h the mixture was concentrated under reduced pressure. The crude (28.5 g) was used without further purification; $^1$H NMR (300 MHz, CDCl$_3$, 300 K) δ [ppm] 7.57 (s, 1H), 4.15 (q, J=7.1, 2H), 2.99-2.91 (m, 6H), 2.60 (m, 2H), 1.25 (t, J=7.1, 3H), 1.02 (t, J=7.4, 3H).

Step 2: 5-Hydrazinylpyrimidine hydrochloride (A2)

In a pressure vessel pyrimidine-5-boronic acid (10 g, 80.7 mmol, 1 eq.), di-tert-butyl-azodicarboxylate (18.6 g, 80.7 mmol, 1 eq.), anhydrous copper(II)acetate (0.5 g, 2.7 mmol, 0.033 eq) in dry methanol (320 mL) were heated at 60° C. for 1 h. The mixture was concentrated in vacuum. The residue was solved in diethyl ether and washed with sat. aq. NaHCO$_3$-sol. and brine. The organic layer was dried over Na$_2$SO$_4$ and concentrated under reduced pressure to yield the intermediate di-tert-butyl 1-(pyrimidin-5-yl)hydrazine-1,2-dicarboxylate.

The intermediate was solved in dioxane (130 mL) and 4M HCl in dioxane (150 mL, 592 mmol, 10.5 eq.) was slowly added. After 30 h at RT, the solid was filtered off and washed twice with diethyl ether. The solid was dried in vacuum yielding A2 (9.3 g, 79%). $^1$H NMR (300 MHz, DMSO, 300 K) δ [ppm] 10.43 (br.s, 1H), 9.05 (br.s, 3H), 8.78 (s, 1H), 8.58 (s, 2H). MS (ES) C$_4$H$_6$N$_4$ requires: 110, found: 111 (M+H)$^+$.

Step 3: Ethyl 5-ethyl-1-(pyrimidin-5-yl)-1H-pyrazole-4-carboxylate (A3)

To a solution of A2 (5.5 g, 37.5 mmol, 1 eq.) in dry EtOH (150 mL) was added Cs$_2$CO$_3$ (12.3 g, 37.5 mmol, 1 eq.). After 10 min at RT, A1 (7.1 g, 35.6 mmol, 0.95 eq.) was added and the mixture was reflux for 7 h. The reaction mixture was filtered and the filtrate was concentrated in vacuum. Water was added and aq. phase was extracted with ethyl acetate. The combined organic phase was dried over MgSO$_4$ and concentrated in vacuo.

The crude product was purified by flash chromatography on silica gel (PE/Et$_2$O=100:0 to 1:1) to yield the desired product A3 (2.86 g, 31%); $^1$H NMR (300 MHz, CDCl$_3$, 300 K) δ [ppm] 9.29 (s, 1H), 8.89 (s, 2H), 8.09 (s, 1H), 4.34 (q, J=7.1 Hz, 2H), 3.00 (q, J=7.5 Hz, 2H), 1.38 (t, J=7.1 Hz, 3H), 1.24 (t, J=7.5 Hz, 3H). MS (ES) C$_{12}$H$_{14}$N$_4$O$_2$ requires: 246, found: 247 (M+H)$^+$.

Step 4: 5-Ethyl-1-(pyrimidin-5-yl)-1H-pyrazole-4-carboxylic acid (A4)

To a solution of A3 (2.3 g, 9.3 mmol, 1.0 eq.) in THF (250 mL) was added a solution of KOH (1.05 g, 18.79 mmol, 2 eq.) in water (250 mL). The mixture was stirred at 55° C. for 18 h and then evaporated in vacuum. The crude was purified by RP-flash chromatography (water, then water/ACN=100:0 to 95:5) yielding A4 (1.7 g, 85%); $^1$H NMR (300 MHz, deuterium oxide, 300 K) δ [ppm] 9.24 (s, 1H), 9.00 (s, 2H), 7.98 (s, 1H), 2.94 (q, J=7.5 Hz, 2H), 1.06 (t, J=7.5 Hz, 3H). MS (ES) C$_{10}$H$_{10}$N$_4$O$_2$ requires: 218, found: 219 (M+H)$^+$.

Step 4: N-(4-((6,7-Dimethoxyquinolin-4-yl)oxy)-3-fluorophenyl)-5-ethyl-1-(pyrimidin-5-yl)-1H-pyrazole-4-carboxamide (A6)

A solution of A4 (1400 mg, 6.42 mmol, 1.2 eq.) in SOCl$_2$ (70 mL) was heated for 3 h at 80° C. Solvents were removed in vacuum, the crude material was resolved in dry toluene and evaporated again under reduced pressure to yield the acid chloride A5. The acid chloride A5 was solved in dry pyridine (50 mL) at 0° C. and 5-((6,7-dimethoxyquinolin-4-yl)oxy)pyridin-2-amine 1 (1680 mg, 5.35 mmol, 1.0 eq.) was added. After stirring at RT for 12 h, water (2 mL) was added and the mixture was evaporated under reduced pressure. The crude product was purified by flash chromatography on silica gel (DCM/MeOH=100:0 to 20:1), followed by RP-HPLC (column: C18), using H$_2$O and ACN as eluents, the desired fractions were lyophilized to afford the titled compound A6 (1.18 g, 2.29 mmol, 43%) as a white powder. In order to prepare the HCl-salt, A6 was solved in ACN (40 mL) and water (20 mL). After adding aq. HCl (c=1 mol/L, 2.29 mmol, 1.0 eq) and stirring for 1 h, the mixture was lyophilized yielding the HCl-salt of A6; $^1$H NMR (400 MHz, DMSO, 300 K) δ [ppm] 10.49 (s, 1H), 9.36 (s, 1H), 9.11 (s, 2H), 8.82 (d, J=6.6 Hz, 1H), 8.57 (s, 1H), 8.13 (dd, J=13.2, 2.2 Hz, 1H), 7.76 (s, 2H), 7.67 (s, 1H), 7.58 (t, J=9.0 Hz, 1H), 6.98 (d, J=6.4 Hz, 1H), 4.04 (s, 6H), 3.02 (q, J=7.5 Hz, 2H), 1.10 (t, J=7.5 Hz, 3H). MS (ES) $C_{27}H_{23}FN_6O_4$ requires: 514, found: 515 (M+H)$^+$.

IC$_{50}$ values of N-(4-((6,7-dimethoxyquinolin-4-yl)oxy)-3-fluorophenyl)-5-ethyl-1-(pyrimidin-5-yl)-1H-pyrazole-4-carboxamide ("A6") according to the invention inhibiting RON

| Compound No. | RON enzyme assay IC$_{50}$ [nM] | RON cell assay IC$_{50}$ [nM] |
|---|---|---|
| "A6" | 30 | 8.1 |

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of NaH$_2$PO$_4$ .2H$_2$O, 28.48 g of Na$_2$HPO$_4$ .12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. The compound N-(4-((6,7-dimethoxyquinolin-4-yl)oxy)-3-fluorophenyl)-5-ethyl-1-(pyrimidin-5-yl)-1H-pyrazole-4-carboxamide

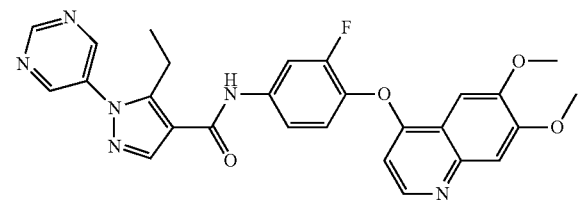 [SMILES: CCc1c(C(=O)Nc2ccc(Oc3ccnc4cc(OC)c(OC)cc34)c(F)c2)cnn1-c1cncnc1]

and pharmaceutically usable salts, tautomers and stereoisomers thereof, including mixtures thereof in all ratios.

2. Process for the preparation of N-(4-((6,7-dimethoxyquinolin-4-yl)oxy)-3-fluorophenyl)-5-ethyl-1-(pyrimidin-5-yl)-1H-pyrazole-4-carboxamide or pharmaceutically usable salts, tautomers or stereoisomers thereof of claim 1, comprising:

reacting

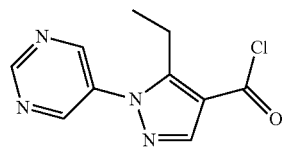 [SMILES: CCc1c(C(=O)Cl)cnn1-c1cncnc1]

with

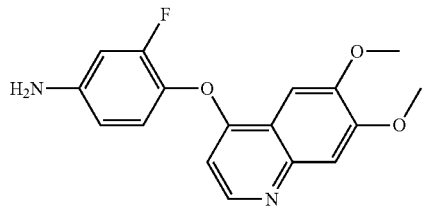 [SMILES: COc1cc2nccc(Oc3ccc(N)cc3F)c2cc1OC]

and/or converting N-(4-((6,7-dimethoxyquinolin-4-yl)oxy)-3-fluorophenyl)-5-ethyl-1-(pyrimidin-5-yl)-1H-pyrazole-4-carboxamide into one of its pharmaceutically usable salts.

3. A pharmaceutical composition comprising N-(4 ((6,7-dimethoxyquinolin-4-yl)oxy)-3-fluorophenyl)-5-ethyl-1-(pyrimidin-5-yl)-1H-pyrazole-4-carboxamide and/or pharmaceutically usable salts, tautomers or stereoisomers thereof, including mixtures thereof in all ratios of claim 1, and optionally one or more excipients and/or adjuvants.

* * * * *